United States Patent
Jackson

(10) Patent No.: US 6,440,170 B1
(45) Date of Patent: Aug. 27, 2002

(54) THREADED INTERBODY DEVICE

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/729,600

(22) Filed: Dec. 4, 2000

(51) Int. Cl.[7] .............................. A61F 2/44; A61B 17/56
(52) U.S. Cl. ...................................... 623/17.16; 606/61
(58) Field of Search ...................... 623/17.11, 17.15, 623/17.16; 606/61

(56) References Cited

U.S. PATENT DOCUMENTS

| | | |
|---|---|---|
| 5,458,638 A | 10/1995 | Kuslich et al. |
| 5,489,308 A | 2/1996 | Kuslich et al. |
| 5,609,636 A | 3/1997 | Kohrs et al. |
| 5,658,337 A | 8/1997 | Kohrs et al. |
| 5,665,122 A | 9/1997 | Kambin |
| 5,669,909 A | 9/1997 | Zdeblick et al. |
| 5,782,919 A | 7/1998 | Zdeblick et al. |
| 5,865,847 A | 2/1999 | Kohrs et al. |
| 5,904,719 A * | 5/1999 | Errico et al. .............. 623/17.16 |
| 6,123,705 A * | 9/2000 | Michelson ................ 623/17.16 |
| 6,206,922 B1 * | 3/2001 | Zdeblick et al. .......... 623/17.11 |

* cited by examiner

Primary Examiner—David J. Isabella
(74) Attorney, Agent, or Firm—John C. McMahon

(57) ABSTRACT

An interbody device having upper and lower surfaces that are sized and shaped to be operably positioned between a pair of adjacent vertebrae for support and/or fusion. The upper and lower surfaces have a generally convex curvature. The upper and lower surfaces are joined by a pair of side surfaces that are arcuate and semi-circular, when viewed from the front, so as to be generally concave. The interbody devices are used in pairs between two vertebrae and joined by a bar that is received in a recess in each of the devices so as to resist rotation of the devices relative to the bar subsequent to installation.

14 Claims, 2 Drawing Sheets

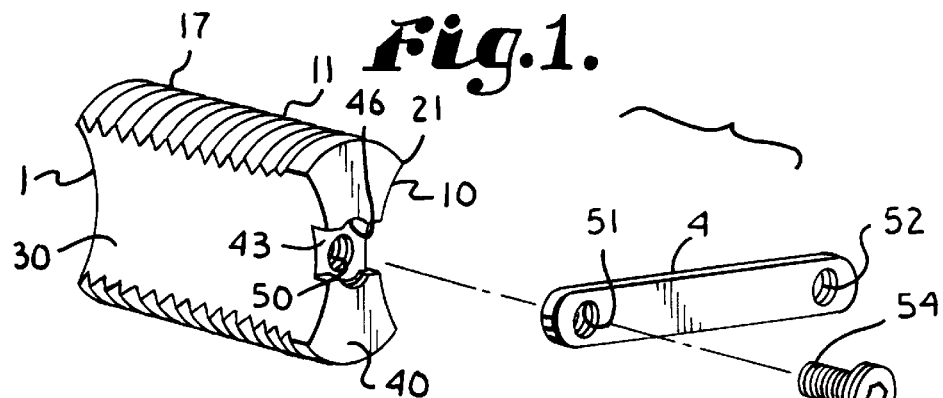
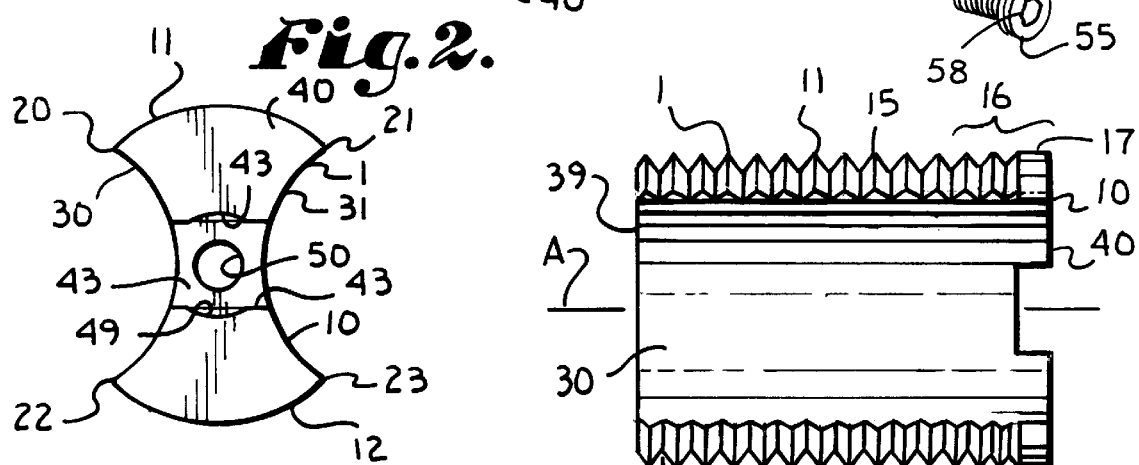
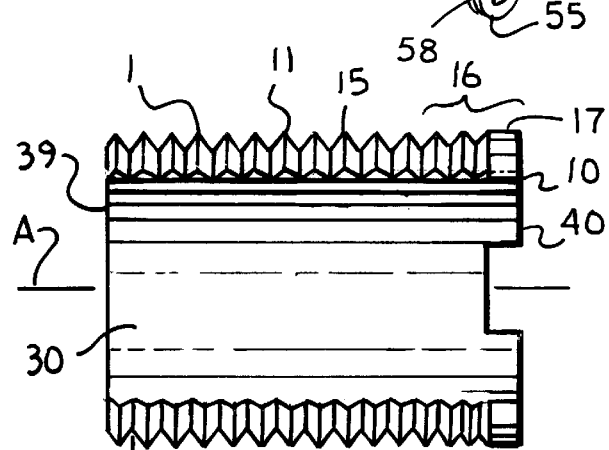
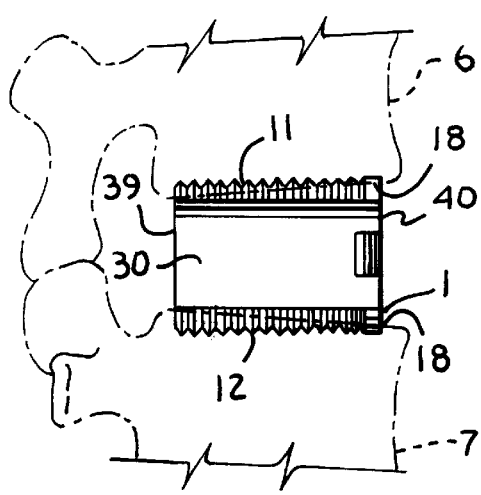
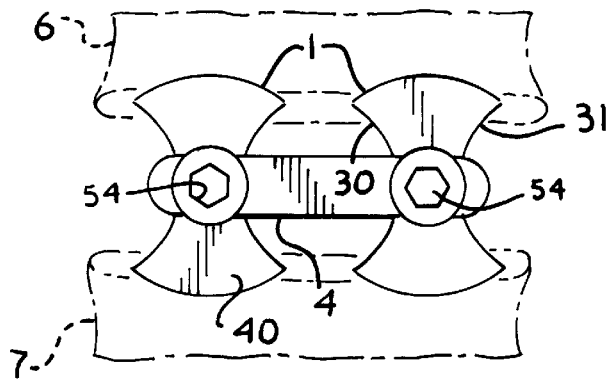

THREADED INTERBODY DEVICE

BACKGROUND OF THE INVENTION

The present application is directed to a threaded interbody device for implantation between a pair of adjacent vertebrae in order to provide support to the vertebrae and/or promote fusion between the vertebrae.

In the human spine the pad or disc between vertebrae is sometimes damaged or deteriorates due to age, disease, injury or congenital defect. The vertebrae themselves may also become compressed or otherwise damaged. Because of this, surgery is often utilized to place spacers or interbody devices between the vertebrae which provide proper spacing of the vertebrae and which often are also utilized to promote fusion between the vertebrae. When a device of this type is utilized for purposes of promoting fusion, it is often referred to as a fusion cage or an intervertebral fusion device. When utilized to promote fusion, the interbody devices often are windowed and packed with bone so as to promote growth of the bone between the vertebrae. Sometimes bone is packed between a pair of devices that are placed in close proximity to one another between the vertebrae so as to promote growth of bone and, therefore, fusion between the vertebrae.

Interbody devices are typically either generally rectangular in shape or generally cylindrical in shape. The cylindrical devices have an advantage that they can be threadably received between and into the bones themselves. For this purpose, the vertebrae are typically first spaced and then a drill is utilized to create a partial bore in each vertebrae which allows the interbody device to be received between the vertebrae. Because of the space between the bones, the interbody device usually engages the bone's only along an upper surface and a lower surface thereof. When the cage is of a cylindrical threaded type, the upper and lower surfaces are curved and essentially designed to engage the portion of the vertebrae whereat bone is unremoved during boring to create an opening for the device.

When interbody devices of this type are used, it is desirable that the device support as much surface of bone as possible to provide strength and reduce the likelihood of subsidence of the device into the bone, especially as part of the bone is spongy by nature. The remainder of the structure mainly functions to support the two surfaces, unless the device is also used as a cage within which to pack bone. Because it is also desirable in such structures to maintain weight and volume as low as possible, in order to make the device more compatible with the body, it is also desirable to make the entire device as small and lightweight as possible, while maintaining strength.

Still further, the cylindrical devices are most often threaded in order to bite into the bone of the vertebrae in order to resist inadvertent removal of the devices from between the vertebrae. Therefore the upper and lower surfaces are threaded for this purpose. In the past flat sided segments have been removed and a tool which saddles over the device has been used that slides along the sides thereof to at least partially complete the threads and that can be rotated to allow the device to be screwed between the vertebrae. Consequently, it is desirable to have a side structure that reduces volume, maintains strength and allows for mating engagement with a tool that can both rotate the device and complete the thread during installation.

Finally, devices of this type that have sectors in the sidewalls missing are essentially taller than wide. This leads to a potential for instability in that the device can inadvertently rotate 90° during use and partly collapse. In order to avoid this, an additional structure is needed to prevent inadvertent rotation of the device once it is installed.

SUMMARY OF THE INVENTION

An interbody or intervertebral spacer device for placement between a pair of spaced but adjacent vertebrae. The device has upper and lower surfaces that are threaded so as to have a helically wound threadform pattern thereon that is discontinuous between the two surfaces, but mateable with a similar threadform on a tool for completion of the thread for use during insertion of the device.

The device has an elongate body that extends along an axis of rotation. The upper and lower surfaces of the body are convex and the two side surfaces are concave in shape. That is, a cross-section of the upper surfaces and lower surfaces and the side surfaces have edges which are generally semi-circular in shape, except that the upper and lower surface are convex or bowed outwardly, whereas the side surfaces are concave or bowed inwardly. Preferably the radii of generation of each of the side surfaces, the upper surface and the lower surface are approximately the same.

The side surfaces join together the outer edges of the upper and lower surfaces on respective sides of the device. In this manner the device has a profile from the front which approximates a double-headed ax.

The devices are utilized in pairs between two adjacent vertebrae. The devices are preferably joined by a bar. Each of the devices has a recess located on the front thereof within which the bar snugly fits such that the bar resists rotation of each device subsequent to installation. This prevents the devices from inadvertently rotating to a non-supporting configuration during use. A set screw joins the bar to each device.

OBJECTS AND ADVANTAGES OF THE INVENTION

Therefore, the objects of the present invention are: to provide an interbody spacer or fusion cage device that is threaded on upper and lower surfaces thereof and can be screwed between a pair of vertebrae in order to support the vertebrae and/or to promote fusion between the vertebrae; to provide such a device having concave arcuate side surfaces that join the upper and lower surfaces on opposite elongate sides of the device; to provide such a device wherein the structure provides strength while reducing volume and weight; to provide such a device wherein the device easily mates with an insertion tool having external threads that align with the threads of the device to allow screwing of the device between a pair of vertebrae; to provide such a device that can be either solid or partly hollow in order to allow packing with bone chips or the like; to provide such a device allowing a relatively close spacing of a pair of devices in side by side relationship; to provide such a device that allows a substantial opening between a pair of devices in side by side relationship to facilitate packing with bone chips and subsequent fusion between the vertebrae associated with the devices; to provide such a device utilized in a pair in conjunction with a bar connecting the pair to resist inadvertent rotation of the devices during use; to provide such a device that includes feathering or reduced thread depth near the front or anterior end of the device to provide an even surface for engagement with a harder bony region near the anterior end of the vertebrae in order to reduce the likelihood of subsidence of the device into the vertebrae after installation; and to provide such a device that is relatively easy to construct, inexpensive to produce and especially well suited for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of an interbody device and a bar for linking the interbody device with a second such device in accordance with the present invention.

FIG. 2 is a front elevational view of the device.

FIG. 3 is a side elevational view of the device.

FIG. 4 is a side elevational view of the device on a reduced scale shown positioned between a pair of vertebrae.

FIG. 5 is a front elevational view on a reduced scale of a pair of the devices joined by the bar and positioned between a pair of vertebrae.

DETAILED DESCRIPTION OF THE INVENTION

Figure 6:
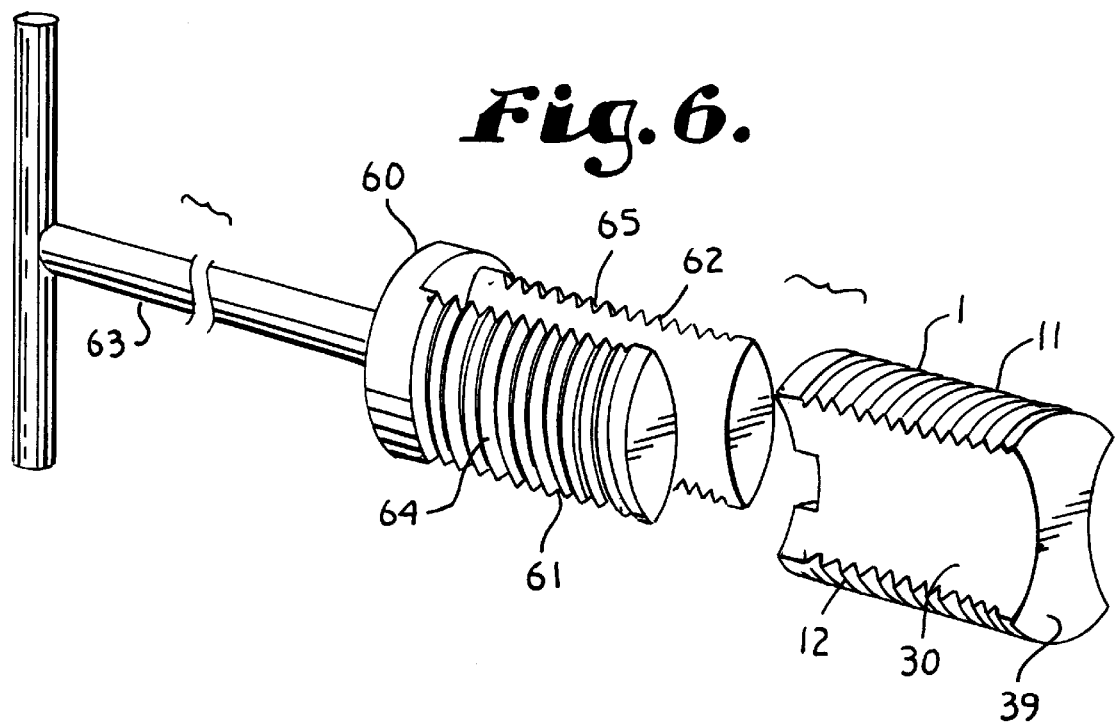
FIG. 6 is a perspective view of the device mated with a tool for installing the device.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates an interbody spacer or device. Normally the device 1 is utilized in pairs and connected with a bar 4 for placement between a pair of adjacent spinal vertebrae 6 and 7.

The device 1 has a generally partial cylindrical shape with equal opposed side portions or sectors removed. In particular, the device 1 has a body 10 with an upper surface 11 and a lower surface 12. The upper and lower surfaces 11 and 12 are semi-cylindrical in shape, elongate and are typically generated from a radii of the same length. The upper and lower surface also have a thread 15 that is wound helically about the device 1 in a pattern that is discontinuous between the upper and lower surfaces 11 and 12. The illustrated thread 15 is a V-shaped thread, although other types of thread forms, such as square or step forms,may be utilized in accordance with the invention.

As is seen in FIG. 3, the thread 15 has a major diameter and minor diameter forming the peaks and valleys of the thread. As the thread approaches the anterior or front end (to the right of FIG. 3) of the device 1 in a region 16 the thread depth reduces progressively with each consecutive turn or 360° pass about the device 1. That is, each time the thread 15 passes once around the device 1 in a turn, the thread depth becomes less and the minor diameter of the thread becomes greater.

Near the very front of the device 1 the minor thread depth and major thread depth are generally equal so as to produce a generally smooth semi-cylindrical region 17. The semi-cylindrical region 17 provides greater support to an anterior harder bony region 18 of the vertebrae 6 and 7 so as to oppose subsidence during usage. The upper surface 11 has opposed parallel edges 20 and 21 and the lower surface 12 has similar parallel edges 22 and 23.

The body 10 also has a pair of side surfaces 30 and 31. The side surfaces 30 extends between the top surface edge 20 and bottom surface edge 22, whereas the side surface 31 extends between the top surface edge 21 and bottom surface edge 23. The side surfaces 30 and 31 are curved, arcuate or crescent shaped, as is seen from the front in FIG. 2. Preferably, the side surfaces 30 and 31 each have a radius of generation which is approximately equal. In some embodiments of the invention, the radius of generation of each of the side surfaces 30 and 31 will be equivalent to the radii of generation of the upper surface 10 and lower surface 11, except the side surfaces 30 and 31 will be concave in nature and the upper and lower surfaces 10 and 11 are convex. In this manner the side surfaces 30 and 31 are the reverse of the surface that would be generated by either the upper or lower surfaces 10 or 11 being continued with the same arc about the exterior of the device 1. Also, the device has an axis of rotation A. Any plane passing through the device 1 that is perpendicular to the axis A has an intersection with any of the surfaces 10, 11, 30 and 31 which is semi-circular.

The body 10 also has a generally flat rear surface 39 and a front surface 40. The front surface 40 has a vertically centrally located recess 43. The recess 43 has an anterior rectangularly shaped portion 45 and an outer portion 46 which is also centrally rectangular in shape, but has semi-circular upper and lower extensions 48 and 49. A threaded bore 50 passes coaxially trough the front surface 40 and is centered on the recess 43.

The bar 4 is elongate with rounded opposite ends. The bar 4 has a pair of apertures 51 and 52. The bar 4 has a cross-section which is sized and shaped to snugly fit in the recess rectangular portion 45 of each device 1. In this manner, the bar 4, when in the respective recesses 43 functions as a lever arm to prevent inadvertent rotation of the devices 1.

A pair of set screws 54 are sized and shaped to be received through respective apertures 51 or 52 in the bar 4 and subsequently, into and threadably received in respective bores 50 of one of the devices 1. Each set screw 54 has a head 55 that is preferably externally threaded and received in a similar thread in the semi-circular shaped portions 48 and 49 of the recess 43. The set screw head 55 also has a coaxially aligned aperture 58 which is sized and shaped to receive a driving tool (not shown) such as an allen wrench. When an allen wrench is to be utilized, the aperture 58 has a hexagonal shaped opening.

Figure 7:
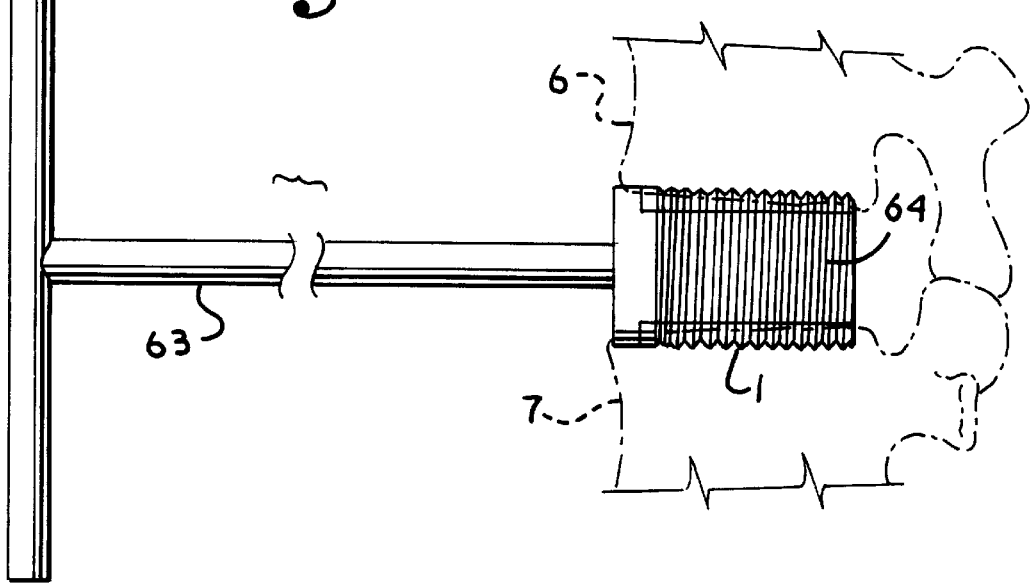
FIG. 7 is a perspective view of the device being installed with the tool between the vertebrae.

In use, a pair of devices 1 are positioned between a pair of vertebrae 6 and 7 such as is shown in FIG. 5. A tool 60 having side panels 61 and 62 includes a handle 63 for turning and is used to insert the devices 1. The side panels 61 and 62 mate with the sides 30 and 31 of each device 1 to complete a cylinder and have external threads 64 and 65 that mate with the thread 15 to complete the thread 15. The device 1 is placed in the tool 60 in the manner shown in FIG. 6 and then inserted between the vertebrae 6 and 7 in the manner shown in FIG. 7. The bar 4 is joined by a pair of set screws 54 to each of the devices 1. Bone chips and the like for promoting growth of bone and fusion between the vertebrae 6 and 7 may be placed between the devices 1, if desired by the surgeon.

It is to be understood that while certain forms of the present invention have been illustrated and described herein, it is not to be limited to the specific forms or arrangement of parts described and shown.

What is claimed and desired to be secured by Letters Patent is as follows:

1. An interbody device for placement between a pair of adjacent vertebrae; said device comprising:
   a) a body having an axis and upper and lower elongate convex surface that are generally coaxially thread depth is reduced; and located with respect to said axis and which are cylindrical in shape along a substantial length of said device; said upper and lower surfaces having elongate side edges;
   b) said body also having inwardly arced concave said surfaces along a substantial length thereof; said side surface extending between respective side edges of said upper and lower surfaces.

2. The device according to claim 1 wherein:
   a) said side surfaces have a semi-circular cross-section in a plane passing perpendicular to said axis.

3. The device according to claim 1 wherein:
   a) both of said side surfaces have a common radius of generation.

4. The device according to claim 3 wherein:
   a) said upper and lower surfaces have a radius of generation approximately equal to said side surfaces common radius of generation.

5. The device according to claim 1 wherein:
   a) said upper and lower surfaces have a helically wound discontinuous thread located thereon.

6. The device according to claim 1 wherein:
   a) said thread extends from a rear to near a front of said device.

7. The device according to claim 6 wherein:
   (a) said thread has a maximum and minimum diameter therealong and said minimum diameter approximately equals said maximum diameter in two forward turns of said thread so as to provide a generally smooth cylindrical surface for anterior bone support.

8. The device according to claim 1 wherein:
   a) said device has a front wall; and
   b) said front wall includes a centrally located recess adapted to receive a bar for connecting together a pair of said devices.

9. The device according to claim 8 in combination with said bar.

10. The combination according to claim 9 wherein:
    a) said recess has upper and lower walls and;
    b) said bar is sized and shaped to snugly abut against said recess walls when placed in said recess so as to resist relative rotation between said bar and said device.

11. The combination according to claim 10 wherein:
    a) said bar includes a bore and said device includes a threaded bore such that both of said bores align when said bar is received in said slot.

12. The combination according to claim 11 including:
    a) a set screw sized and shaped to be received through said bar bore and threaded to be matingly received in said device threaded bore to operably secure said bar to said device.

13. An interbody device for placement between a pair of adjacent vertebrae; said device comprising:
    (a) a body having an axis and upper and lower elongate surfaces that are generally coaxially located with respect to said axis; said upper and lower surfaces having elongate side edges; said upper and lower surfaces each having a thread located thereon;
    (b) said thread has a generally uniform thread depth except near a front of said device whereat said thread depth is reduced; and
    (c) said body also having inwardly arced side surfaces; said side surfaces extending between respective side edges of said upper and lower surfaces.

14. In a threaded interbody device for placement between a pair of adjacent vertebrae having an axis of rotation with upper and lower outer surfaces with threads thereon adapted to operably engage respective vertebrae and a pair of concave cylindrically shaped side surfaces joining respective outer edges of said lower and upper surfaces; the improvement comprising wherein:
    (a) each of said upper and lower surfaces are sectors of a cylinder substantially along the entire length of said device and have a convex circular cross-section in a plane perpendicular to said axis.

* * * * *

UNITED STATES PATENT AND TRADEMARK OFFICE
CERTIFICATE OF CORRECTION

PATENT NO.   : 6,440,170 B1
DATED        : August 27, 2002
INVENTOR(S)  : Roger P. Jackson It is certified that error appears in the above-identified patent and that said Letters Patent is hereby corrected as shown below:

<u>Column 5,</u>
Lines 7 - 19, should read as follows:
-- 1. An interbody device for placement between a pair of adjacent vertebrae; said device comprising:
   a) a body having an axis and upper and lower elongate convex surfaces
      that are generally coaxially located with respect to said axis
      and which are cylindrical in shape along a substantial length of said device; said
      upper and lower surfaces having elongate side edges;

b) said body also having inwardly arced concave side surfaces along
      a substantial length thereof; said side surfaces extending
      between respective side edges of said upper and lower surfaces. --

Signed and Sealed this

Twenty-fourth Day of December, 2002

JAMES E. ROGAN
*Director of the United States Patent and Trademark Office*